US008648906B2

(12) United States Patent
Delaney

(10) Patent No.: US 8,648,906 B2
(45) Date of Patent: Feb. 11, 2014

(54) PRECISION SOLDER RESIST REGISTRATION INSPECTION METHOD

(75) Inventor: Mark Lawrence Delaney, Shoreline, WA (US)

(73) Assignee: Mitutoyo Corporation, Kawasaki-shi (JP)

( * ) Notice: Subject to any disclaimer, the term of this patent is extended or adjusted under 35 U.S.C. 154(b) by 579 days.

(21) Appl. No.: 12/904,013

(22) Filed: Oct. 13, 2010

(65) Prior Publication Data

US 2012/0092488 A1  Apr. 19, 2012

(51) Int. Cl.
    *H04N 7/18* (2006.01)
(52) U.S. Cl.
    USPC .......................... 348/128; 356/123; 356/4.05
(58) Field of Classification Search
    CPC ....................................................... H04N 7/18
    USPC ..................... 348/84–86, 125–135
    See application file for complete search history.

(56) References Cited

U.S. PATENT DOCUMENTS

| | | | |
|---|---|---|---|
| 5,039,868 A | 8/1991 | Kobayashi | |
| 5,064,291 A * | 11/1991 | Reiser | 356/625 |
| 6,542,180 B1 | 4/2003 | Wasserman | |
| 7,324,682 B2 | 1/2008 | Wasserman | |
| 7,454,053 B2 | 11/2008 | Bryll | |
| 2005/0109959 A1* | 5/2005 | Wasserman et al. | 250/559.19 |
| 2008/0100829 A1* | 5/2008 | Watson | 356/123 |
| 2008/0186481 A1* | 8/2008 | Chen | 356/237.1 |
| 2010/0158343 A1 | 6/2010 | Bryll | |
| 2010/0163729 A1* | 7/2010 | Isozaki | 250/310 |

OTHER PUBLICATIONS

Campbell, S.R., "Autofocus Video Tool and Method for Precise Dimensional Inspection," U.S. Appl. No. 12/608,943, filed Oct. 29, 2009.
Kobayashi, H.H., et al., "Hybrid Defect Detection Method Based on the Shape Measurement and Feature Extraction for Complex Patterns," IEICE Transactions on Information and Systems E83-D(7):1338-1345, Jul. 2000.
Moganti, M., et al., "Automatic PCB Inspection Algorithms: A Survey," Computer Vision and Image Understanding 63(2):287-313, Mar. 1996.
"QVPAK 3D CNC Vision Measuring Machine: Operation Guide," Version 2.0, Manual No. 4911GB, Series No. 359, Mitutoyo Corporation & Micro Encoder Inc., Kanagawa, Japan, Sep. 1996, 86 pages.
"QVPAK 3D CNC Vision Measuring Machine: User's Guide," Version 7.1, 2d ed., Manual No. 99MCB225A1, Series No. 359, Mitutoyo Corporation & Micro Encoder Inc., Kanagawa, Japan, Sep. 2003, 370 pages.

* cited by examiner

*Primary Examiner* — Tung Vo
*Assistant Examiner* — Obafemi Sosanya
(74) *Attorney, Agent, or Firm* — Christensen O'Connor Johnson Kindness PLLC

(57) ABSTRACT

A method is disclosed for operating a machine vision inspection system to determine a fluorescent imaging height for acquiring a fluorescent image for repeatably determining the location of a feature within the fluorescent material. The height of an exposed workpiece portion exposed outside of the fluorescent material is determined (e.g., using a height sensor or autofocus operations). The determined height is repeatable. The exposed portion has a characteristic height relative to the fluorescent material and/or features located therein. The fluorescent imaging height, which may be inside the fluorescent material, is determined relative to the determined height of the exposed portion. The fluorescent imaging height is determined such that it enhances the detection of the desired feature located within the fluorescent material in the resulting fluorescent image. For a variety of workpieces, the method provides automatic acquisition of appropriately focused fluorescent image more reliably than previously known methods.

21 Claims, 6 Drawing Sheets

PRECISION SOLDER RESIST REGISTRATION INSPECTION METHOD

FIELD OF THE INVENTION

The invention relates generally to machine vision inspection systems, and more particularly to methods of inspecting workpiece features located within fluorescent material.

BACKGROUND

Precision machine vision inspection systems (or "vision systems" for short) can be utilized to obtain precise dimensional measurements of inspected objects and to inspect various other object characteristics. Such systems may include a computer, a camera and optical system, and a precision stage that is movable in multiple directions so as to allow the camera to scan the features of a workpiece that is being inspected. One exemplary prior art system that is commercially available is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the *QVPAK 3D CNC Vision Measuring Machine User's Guide*, published January 2003, and the *QVPAK 3D CNC Vision Measuring Machine Operation Guide*, published September 1996, each of which is hereby incorporated by reference in their entirety. This product, as exemplified by the QV-302 Pro model, for example, is able to use a microscope-type optical system to provide images of a workpiece at various magnifications, and move the stage as necessary to traverse the workpiece surface beyond the limits of any single video image. A single video image typically encompasses only a portion of the workpiece being observed or inspected, given the desired magnification, measurement resolution, and physical size limitations of such systems.

Machine vision inspection systems generally utilize automated video inspection. U.S. Pat. No. 6,542,180 (the '180 patent) teaches various aspects of such automated video inspection and is incorporated herein by reference in its entirety. As taught in the '180 patent, automated video inspection metrology instruments generally have a programming capability that allows an automatic inspection event sequence to be defined by the user for each particular workpiece configuration. This can be implemented by text-based programming, for example, or through a recording mode which progressively "learns" the inspection event sequence by storing a sequence of machine control instructions corresponding to a sequence of inspection operations performed by a user with the aid of a graphical user interface, or through a combination of both methods. Such a recording mode is often referred to as "learn mode" or "training mode." Once the inspection event sequence is defined in "learn mode," such a sequence can then be used to automatically acquire (and additionally analyze or inspect) images of a workpiece during "run mode."

The machine control instructions including the specific inspection event sequence (i.e., how to acquire each image and how to analyze/inspect each acquired image) are generally stored as a "part program" or "workpiece program" that is specific to the particular workpiece configuration. For example, a part program defines how to acquire each image, such as how to position the camera relative to the workpiece, at what lighting level, at what magnification level, etc. Further, the part program defines how to analyze/inspect an acquired image, for example, by using one or more video tools such as edge/boundary detection video tools.

Video tools (or "tools" for short) and other graphical user interface features may be used manually to accomplish manual inspection and/or machine control operations (in "manual mode"). Their set-up parameters and operation can also be recorded during learn mode, in order to create automatic inspection programs, or "part programs." Video tools may include, for example, edge/boundary detection tools, autofocus tools, shape or pattern matching tools, dimension measuring tools, and the like.

One application for a machine vision inspection system is inspection of a printed circuit board (PCB), wherein it may be desirable to measure the registration relationship between a pattern in a solder resist layer and conductive features intended to be exposed and/or insulated by the solder resist layer. Prior art methods for measuring solder resist registration are neither fast enough, nor precise enough, nor robust enough, to reliably meet the inspection requirements for the increasingly small features present in current or future generations of PCB technology. Some solder resists comprise fluorescent material. Some known machine vision inspection systems are capable of imaging with light which does not cause fluorescent workpiece features to fluoresce and light which does cause fluorescent workpiece features to fluoresce. For example, U.S. Pat. No. 5,039,868 (the '868 patent) discloses such an inspection system. However, the '868 patent generally relates to pattern recognition of features on a printed circuit board and does not address focusing operations and means for generating high resolution and highly repeatable measurements of workpiece feature edge locations obscured by solder resist layer, and/or related edge spacings or the like, which may need to be measured with accuracy on the order of 10 microns or less. Improvements in inspection methods related to locating features intended to be exposed and/or insulated by a fluorescent material layer, such as a solder resist layer, would be desirable.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method is provided for operating a machine vision inspection system to determine a reliable and repeatable fluorescent imaging height, such as may be used for acquiring a fluorescent image for accurately and repeatably determining the location of a workpiece edge that is to be inspected within a fluorescent material (e.g., a layer of fluorescent material). In one application, the method may be used as part of a process to measure a registration or overlap dimension of a solder resist layer relative to a conductive element that it covers on a printed circuit board.

The method, in various embodiments may comprise steps including: (a) positioning an exposed portion of a surface of the workpiece such that its height may be determined by the machine vision inspection system, wherein the exposed portion is not covered by the layer of fluorescent material and has a characteristic surface height along a focus axis relative to a height within the layer of fluorescent material; (b) configuring the machine vision inspection system to determine the height of the exposed portion; (c) determining the height of the exposed portion; (d) determining a fluorescent imaging height to be used for fluorescent imaging of the workpiece feature edge that is located within the layer of fluorescent material, wherein the fluorescent imaging height is determined in relation to the determined height of the exposed portion; and performing at least one of (e) and (f), wherein (e) comprises storing the determined fluorescent imaging height in association with a part program for later use when acquiring a fluorescent image that is used for inspecting the workpiece feature edge that is located within the layer of fluorescent material (e.g., the workpiece feature edge represents a corresponding workpiece feature edge that is located within a corresponding layer of fluorescent material on a corresponding workpiece that is inspected using the part program), and (f) comprises using the fluorescent imaging height determined in relation to the determined height of the exposed portion during execution of a part program when acquiring a fluorescent image that is used for inspecting the workpiece feature edge that is located within the layer of fluorescent material.

In some embodiments, the workpiece is a representative workpiece and the method is performed in association with a learn mode of operation of the machine vision inspection system, which is used for creating a part program to be used for inspecting workpieces similar to the representative workpiece, and the method comprises performing steps (a), (b), (c), (d) and (e). In some embodiments, the method performed in learn mode may further include steps of: (g) positioning the workpiece feature edge that is located within the layer of fluorescent material in the field of view of the machine vision inspection system; (h) positioning the machine vision inspection system at the determined fluorescent imaging height; (i) illuminating the field of view using an excitation wavelength profile which causes the fluorescent material to fluoresce and output fluorescent imaging light; (j) acquiring a fluorescent image of the field of view using the fluorescent imaging height while illuminating the field of view using the excitation wavelength profile; and (k) determining a location of the workpiece feature edge that is located within the fluorescent material, based on a location of a corresponding intensity change in the fluorescent image. In some embodiments, steps (g), (h), (i), and (j) may be performed as part of step (d), in order to evaluate the results and refine a preliminary estimate of the determined fluorescent imaging height. In some embodiments, step (k) may also be performed as part of step (d), in order to evaluate edge detection results and possibly determine a more effective fluorescent imaging height in step (d). In other applications, steps (g), (h), (i), and (j), and in some cases (k) may be performed simply to evaluate and confirm the effectiveness of the fluorescent imaging height determined in step (d). In some learn mode embodiments, step (k) comprises configuring the parameters of an edge detection video tool, and using that video tool in order to determine the location of the workpiece feature edge on the representative workpiece, and the method further comprises a step (l) which includes storing the configured parameters of the edge detection video tool in association with the part program, for later use to determine the location of the workpiece feature edge in fluorescent images of workpieces similar to the representative workpiece.

In some embodiments, the method is performed in association with a run mode of operation of the machine vision inspection system by executing a part program that includes inspecting the workpiece feature edge that is located within the fluorescent material on a workpiece that is similar to a representative workpiece used to create the part program, and the method comprises performing steps (a), (b), (c), (d) and (f). In such embodiments, in step (d) determining the fluorescent imaging height to be used for fluorescent imaging of the workpiece feature edge may comprise recalling fluorescent imaging height information stored in association with that workpiece feature edge in the part program, and determining the fluorescent imaging height based on that information. For example, in various embodiments the fluorescent imaging height may be determined and stored in the part program as an offset dimension in relation to the determined height of the exposed portion during learn mode. Then, during run mode, the offset dimension may be recalled and added to the determined height of the exposed portion determined during run mode in order to determine the fluorescent imaging height used during run mode. In some embodiments, the fluorescent imaging height is determined to be the same as the determined height of the exposed portion (e.g., the offset dimension is absent, or zero).

In various embodiments, the method performed in run mode may further include the steps of: (g) positioning the workpiece feature edge that is located within the layer of fluorescent material in the field of view of the machine vision inspection system; (h) positioning the machine vision inspection system at the determined fluorescent imaging height; (i) illuminating the field of view using an excitation wavelength profile which causes the fluorescent material to fluoresce and output fluorescent imaging light; (j) acquiring a fluorescent image of the field of view using the fluorescent imaging height while illuminating the field of view using the excitation wavelength profile; and (k) determining a location of the workpiece feature edge that is located within the fluorescent material, based on a location of a corresponding intensity change in the fluorescent image. In some run mode embodiments, step (k) comprises configuring an edge detection video tool of the machine vision inspection system according to associated parameters stored in the part program, and using that edge detection video tool in order to determine the location of the workpiece feature edge in the fluorescent image.

In some embodiments that include performing step (k), the method may further comprise steps (m) determining the location of an edge of the layer of fluorescent material; and (n) determining a measurement of a dimensional relationship between the location of the edge of the layer of fluorescent material layer and the location of the workpiece feature edge that is obscured beneath the layer of fluorescent material. In some such embodiments, the edge of the layer of fluorescent material may advantageously be an edge adjacent to the exposed portion, and an image of that edge may be provided using the first configuration of the machine vision inspection system established in step (b), and the edge of the layer of fluorescent material may be determined in that image. In other such embodiments, the edge of the layer of fluorescent material advantageously included in the fluorescent image of the field of view acquired in step (j), and the edge of the layer of fluorescent material may be determined in that image.

In some embodiments (e.g., when the camera of the machine vision inspection system is sensitive to a wavelength of the excitation wavelength profile), the machine vision inspection system may comprise a fluorescent imaging filter that blocks at least that wavelength of an excitation wavelength profile used as illumination when acquiring a fluorescent image and passes at least one wavelength of the fluorescent imaging light emitted by the fluorescent material, and in step (j) acquiring the fluorescent image comprises using the fluorescent imaging filter to filter the image light used to form the fluorescent image (e.g., by inserting the fluorescent imaging filter into the imaging path). By blocking the excitation light reflected from various surfaces, the features illuminated by fluorescence within the fluorescent material are more clearly seen in the resulting image.

For the best accuracy and reliability in certain applications, it may be advantageous to use an embodiment of the method wherein the fluorescent imaging height is determined such that it falls within the layer of fluorescent material, and/or wherein the exposed portion of the surface of the workpiece has a surface height that falls within a height dimension of the layer of fluorescent material, and/or the exposed portion of the surface of the workpiece is selected such that it is nominally located at the same surface height as a surface of a material layer that has the workpiece feature edge that is obscured beneath the fluorescent material, although implementing these features may not be possible, or even desirable, in all applications.

In some embodiments, the machine vision inspection system comprises a surface height sensor comprising one of a touch probe type sensor, an optical triangulation type sensor, and a focus signal sensor, and step (a) may comprise positioning the exposed portion in a working range of the surface height sensor, step (b) may comprise configuring the machine vision inspection system to use the surface height sensor to determine the height of the exposed portion, and step (c) may comprise using the surface height sensor to determine the height of the exposed portion.

In some embodiments (e.g., when a height sensor is not used for determining the height of the exposed portion), step (a) may comprise positioning the exposed portion in a field of view of the machine vision inspection system, step (b) may comprise configuring the machine vision inspection system in a first configuration to provide an image of at least the exposed portion, and step (c) may comprise determining a focus height of the exposed portion based on images of the exposed portion acquired at different heights while the machine vision inspection system is in the first configuration and using that focus height as the determined height of the exposed portion.

In some embodiments, the machine vision inspection system comprises controllable lighting that can output not only the excitation wavelength profile that is used for fluorescent imaging, but also a non-excitation wavelength profile which illuminates the workpiece such that the workpiece provides primarily reflected image light and an insignificant amount of fluorescent light. In some embodiments, the non-excitation wavelength profile is used in the first configuration for imaging the exposed portion. However, since the exposed portion is not located within the fluorescent material and does not fluoresce, in other embodiments the excitation wavelength profile may be used in the first configuration to provide usable images of the surface of the exposed portion.

In various embodiments disclosed herein, a fluorescent imaging height to be used for imaging features within a fluorescent material based on its fluorescent light is determined in relation to the determined height of a non-fluorescent exposed portion of a surface) that is imaged based on reflected illumination. In other words, the "exposed" portion of the surface is not covered with a fluorescent material. Such embodiments allow improved reliability, repeatability and/or accuracy when imaging and inspecting workpiece features located within a layer of fluorescent material, such as may be desirable or required for solder resist registration measurements that increasingly have tolerances on the order of microns, or other applications including vision-based inspection within fluorescent materials.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
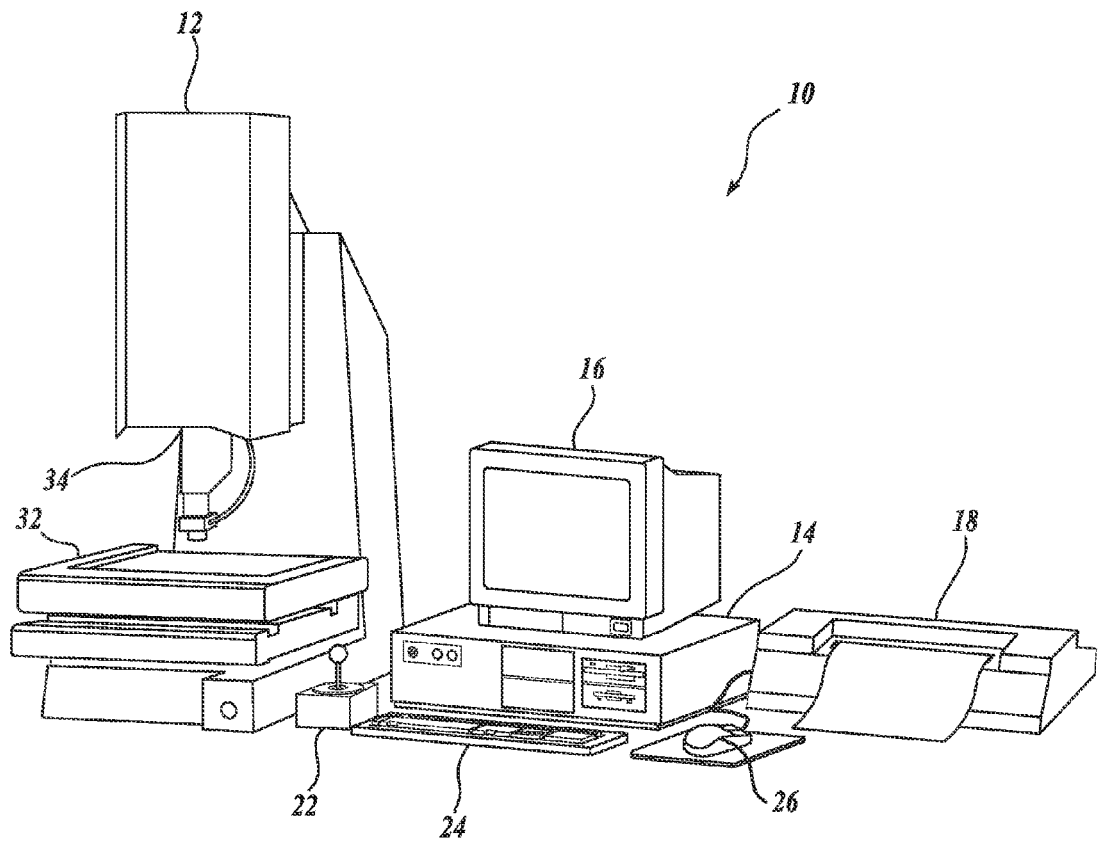
FIG. 1 is a diagram showing various typical components of a general purpose precision machine vision inspection system.

FIG. 1 is a block diagram of one exemplary machine vision inspection system 10 usable in accordance with methods described herein. The machine vision inspection system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the machine vision inspection system 10.

The vision measuring machine 12 includes a moveable workpiece stage 32 and an optical imaging system 34 which may include a zoom lens or interchangeable lenses. The zoom lens or interchangeable lenses generally provide various magnifications for the images provided by the optical imaging system 34. The machine vision inspection system 10 is generally comparable to the QUICK VISION® series of vision systems and the QVPAK® software discussed above, and similar state-of-the-art commercially available precision machine vision inspection systems. The machine vision inspection system 10 is also described in commonly assigned U.S. Pat. Nos. 7,454,053, 7,324,682, U.S. patent application Ser. No. 12/343,383, filed Dec. 23, 2008, and Ser. No. 12/608,943, filed Oct. 29, 2009, which are each incorporated herein by reference in their entireties.

The machine vision inspection system 10 may be configured for imaging and measuring workpiece features which fluoresce under appropriate excitation light, as well as for imaging and measuring combinations of workpiece surface features which do not fluoresce and workpiece surface features which do fluoresce, as outlined in greater detail below.

Figure 2:
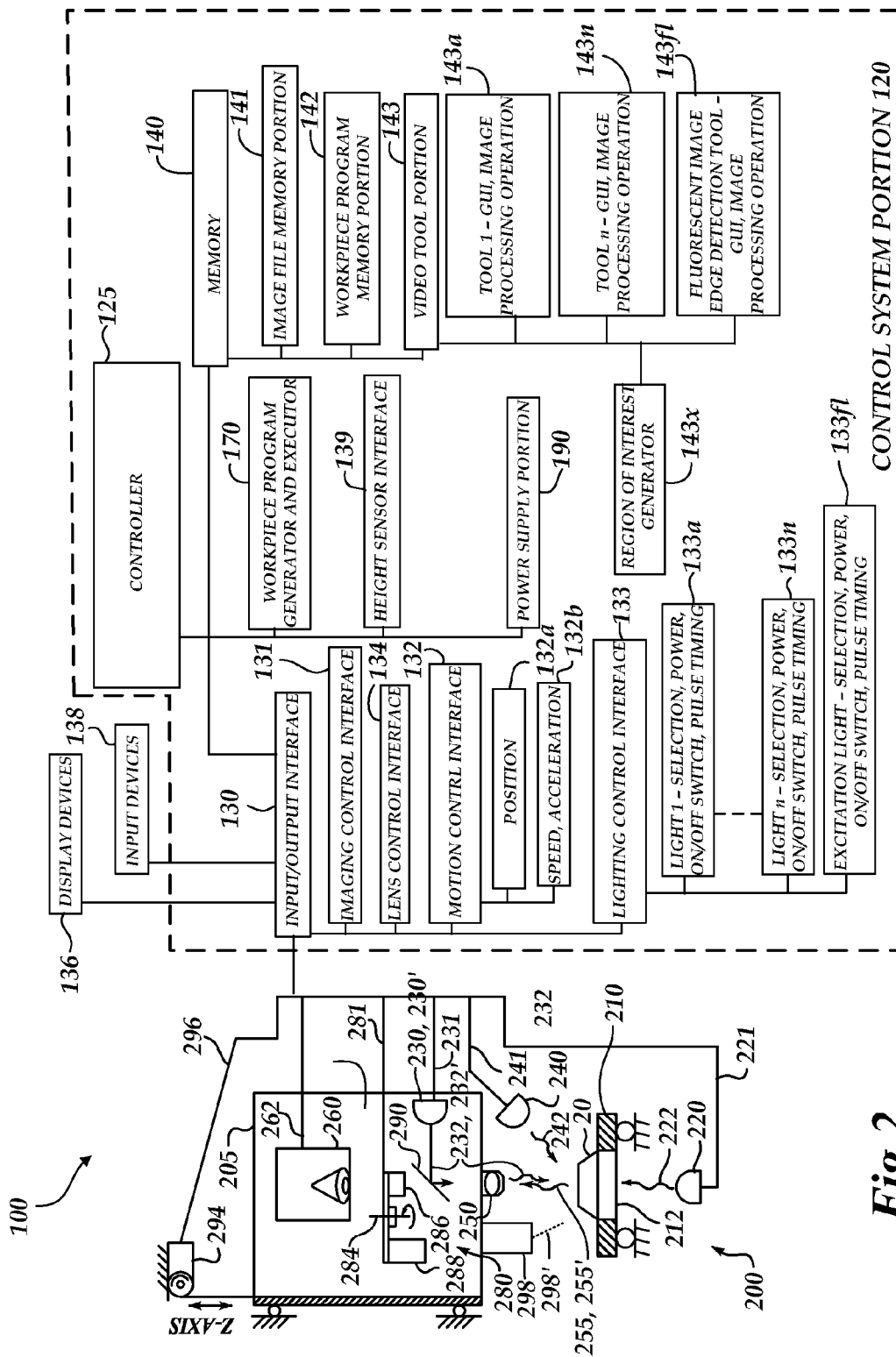
FIG. 2 is a block diagram of a control system portion and a vision components portion of the machine vision inspection system of FIG. 1.

FIG. 2 is a block diagram of a control system portion 120 and a vision components portion 200 of a machine vision inspection system 100. As will be described in more detail below, the control system portion 120 is utilized to control the vision components portion 200. The vision components portion 200 includes an optical assembly portion 205, light sources 220, 230, 230', and 240, and a workpiece stage 210 having a central transparent portion 212. The workpiece stage 210 is controllably movable along X and Y axes that lie in a plane that is generally parallel to the surface of the stage where a workpiece 20 may be positioned. The optical assembly portion 205 includes a camera system 260, an interchangeable objective lens 250, and may include a turret lens assembly 280 having lenses 286 and 288. Alternatively to the turret lens assembly, a fixed or manually interchangeable magnification-altering lens, or a zoom lens configuration, or the like, may be included. The optical assembly portion 205 is controllably movable along a Z-axis that is generally orthogonal to the X and Y axes, by using a controllable motor 294, as described further below. In some embodiments, an optional surface height sensor 298 may be included in, or attached to, the optical assembly portion 205. In some embodiments, the surface height sensor 298 may be distinct from other components of the optical assembly portion 205 sensor. In other embodiments, it may share certain components with other systems. For example, in some embodiments, it may project and/or receive light through the objective lens 250. In any case, the surface height sensor 298 may be configured to use its schematically illustrated height sensing means 298' to determine the height of surface portion of the workpiece 20 along the Z axis or focus direction. In some cases, the surface height sensor 298 works in combination with the Z axis motion control system to determine the height of the surface portion. The optional surface height sensor is described in greater detail below, with reference to FIG. 3.

A workpiece 20, or a tray or fixture holding a plurality of workpieces 20, which is to be imaged using the machine vision inspection system 100 is placed on the workpiece stage 210. The workpiece stage 210 may be controlled to move relative to the optical assembly portion 205, such that the interchangeable objective lens 250 moves between locations on a workpiece 20, and/or among a plurality of workpieces 20. One or more of a stage light 220, a first coaxial light 230, a second coaxial light 230', and a surface light 240 (e.g., a ring light) may emit source light 222, 232, 232' and/or 242, respectively, to illuminate the workpiece or workpieces 20. The light sources 230 and 230' may emit light 232 and 232' along a path including a mirror 290, as described in greater detail with reference to FIG. 3. The second coaxial light 230' may emit source light 232' which has a wavelength profile which causes certain workpiece materials (e.g., solder resist) to fluoresce, as will be discussed in greater detail below. The source light is reflected or transmitted as workpiece light 255, or fluorescent workpiece light 255' is emitted, and the workpiece light used for imaging passes through the interchangeable objective lens 250 and the turret lens assembly 280 and is gathered by the camera system 260. The image of the workpiece(s) 20, captured by the camera system 260, is output on a signal line 262 to the control system portion 120. The light sources 220, 230, 230', and 240 may be connected to the control system portion 120 through signal lines or buses 221, 231, and 241, respectively. To alter the image magnification, the control system portion 120 may rotate the turret lens assembly 280 along axis 284 to select a turret lens, through a signal line or bus 281.

In various exemplary embodiments, the optical assembly portion 205 is movable in the vertical Z-axis direction relative to the workpiece stage 210 using a controllable motor 294 that drives an actuator, a connecting cable, or the like, to move the optical assembly portion 205 along the Z-axis to change the focus of the image of the workpiece 20 captured by the camera system 260. The term Z-axis, as used herein, refers to the axis that is intended to be used for focusing the image obtained by the optical assembly portion 205. The controllable motor 294, when used, is connected to the input/output interface 130 via a signal line 296.

As shown in FIG. 2, in various exemplary embodiments, the control system portion 120 includes a controller 125, the input/output interface 130, a memory 140, a workpiece program generator and executor 170, and a power supply portion 190. Each of these components, as well as the additional components described below, may be interconnected by one or more data/control buses and/or application programming interfaces, or by direct connections between the various elements.

The input/output interface 130 includes an imaging control interface 131, a motion control interface 132, a lighting control interface 133, a lens control interface 134, and a height sensor interface 139 in embodiments that include the surface height sensor 298. The motion control interface 132 may include a position control element 132a, and a speed/acceleration control element 132b. However, it should be appreciated that in various exemplary embodiments, such elements may be merged and/or indistinguishable. The lighting control interface 133 includes lighting control elements 133a-133n, and 133fl which control, for example, the selection, power, on/off switch, and strobe pulse timing if applicable, for the various corresponding light sources of the machine vision inspection system 100. The lighting control element 133fl may control the selection, power, on/off switch, and strobe pulse timing if applicable, for the second coaxial light 230' which may excite fluorescent workpiece materials to emit fluorescent image light. The height sensor interface 139 may exchange control and/or measurement signals with the surface height sensor 298 and/or other elements over a control and signal bus (not specifically shown).

The memory 140 includes an image file memory portion 141, a workpiece program memory portion 142 that may include one or more part programs, or the like, and a video tool portion 143. The video tool portion 143 includes tool portion 143a and other similar tool portions (e.g., 143n), and may include a fluorescent image edge detection tool 143fl in some embodiments, which determine the GUI, image processing operation, etc., for each of the corresponding tools. The video tool portion 143 also includes a region of interest generator 143x that supports automatic, semi-automatic and/or manual operations that define various ROIs that are operable in various video tools included in the video tool portion 143.

In general, the memory portion 140 stores data usable to operate the vision system components portion 200 to capture or acquire an image of the workpiece 20 such that the acquired image of the workpiece 20 has desired image characteristics. The memory portion 140 may also store inspection result data, may further store data usable to operate the machine vision inspection system 100 to perform various inspection and measurement operations on the acquired images (e.g., implemented, in part, as video tools), either manually or automatically, and to output the results through the input/output interface 130. The memory portion 140 may also contain data defining a graphical user interface operable through the input/output interface 130.

The signal lines or buses 221, 231, and 241 of the stage light 220, the coaxial lights 230 and 230', and the surface light 240, respectively, are all connected to the input/output interface 130. The signal line 262 from the camera system 260 and the signal line 296 from the controllable motor 294 are connected to the input/output interface 130. In addition to carrying image data, the signal line 262 may carry a signal from the controller 125 that initiates image acquisition.

One or more display devices 136 (e.g., the display 16 of FIG. 1) and one or more input devices 138 (e.g., the joystick 22, keyboard 24, and mouse 26 of FIG. 1) can also be connected to the input/output interface 130. The display devices 136 and input devices 138 can be used to display a user interface, which may include various graphical user interface (GUI) features that are usable to perform inspection operations, and/or to create and/or modify part programs, to view the images captured by the camera system 260, and/or to directly control the vision system components portion 200.

In various exemplary embodiments, when a user utilizes the machine vision inspection system 100 to create a part program for the workpiece 20, the user generates part program instructions either by explicitly coding the instructions automatically, semi-automatically, or manually, using a workpiece programming language, and/or by generating the instructions by operating the machine vision inspection system 100 in a learn mode to provide a desired image acquisition training sequence. For example, a training sequence may comprise positioning a workpiece feature of a representative workpiece in the field of view (FOV), setting light levels, focusing or autofocusing, acquiring an image, and providing an inspection training sequence applied to the image (e.g., using video tools). The learn mode operates such that the sequence(s) are captured or recorded and converted to corresponding part program instructions. These instructions, when the part program is executed, will cause the machine vision inspection system to reproduce the trained image acquisition and inspection operations to automatically inspect a workpiece or workpieces matching the representative workpiece used when creating the part program.

These analysis and inspection methods that are used to inspect features in a workpiece image are typically embodied in various video tools included in the video tool portion 143 of the memory 140. Many known video tools, or "tools" for short, are included in commercially available machine vision inspection systems, such as the QUICK VISION® series of vision systems and the associated QVPAK® software, discussed above.

It is a particular problem in general purpose machine vision inspection systems, to provide methods and tools that allow relatively unskilled users to program such systems with robust inspection operations that reliably provide accurate measurements. This is particularly true with respect to inspecting features obscured under a fluorescent coating (e.g., a solder resist layer). For example, such coatings may be translucent, and/or may include particulate filler materials, such that prior art precision autofocus operations have failed to reliably provide a desirably focused image (particularly for features underlying or within the fluorescent material) when using conventional illumination and focus methods. In addition, when using fluorescent imaging techniques, the fluorescent material emits light throughout its volume, such that there is no precisely defined focus height for the images arising from such emitted light. Thus, prior art methods have not supported precise and reliable focusing for inspection image acquisition for inspecting features obscured under a fluorescent coating, particularly when it is desired to program the method on one representative workpiece (e.g., during learn mode operations) and then obtain reliable inspection results on similar workpieces that are subject to significant fluorescent material production variations. This problem is further aggravated in that tolerances for solder resist registration errors, and the like, are continually shrinking, such that related inspection repeatability and accuracy for features located within fluorescent materials is desirably on the order of 10 microns, or less, in some applications. Prior art methods of focusing, image acquisition, and image analysis have not provided reliable and robust inspection solutions at these accuracy levels. Various system features and/or methods, disclosed herein, reliably solve such type of measurement problem. In particular, automatic focusing criteria and methods are provided that provide a fluorescent image that indicates an underlying edge feature location (e.g., of a non-fluorescent material that is located within the fluorescent material) with good repeatability and accuracy.

In some embodiments, methods disclosed herein may be implemented by operations that use known components and/or video tools (e.g., autofocus tools and edge detection tools). However, in other embodiments, the methods disclosed herein may be implemented by including a specialized fluorescent image edge detection tool such as the fluorescent image edge detection tool 143fl. For example, the fluorescent image edge detection tool 143fl may be configured to implement fluorescent image focusing user interface features and/or criteria and methods as disclosed herein, in order to allow a relatively unsophisticated user to operate the machine vision inspection system 100 reliably and repeatably to measure an edge of a workpiece feature that is located within the fluorescent material. In some applications, this may allow the determination of precise dimensional relationships between such an edge and a nearby edge of the fluorescent material (e.g., for measuring the registration of a patterned fluorescent material, such as a solder resist layer, relative to an underlying feature). The fluorescent image edge detection tool 143fl may be especially suited for the inspection of PCB's (e.g., to measure related to the solder resist registration relative to underlying features on the PCB's). Automatic fluorescent image focusing features, criteria and operations usable separately, or in association with the fluorescent image edge detection tool 143fl, are discussed in greater detail below.

Figure 3:
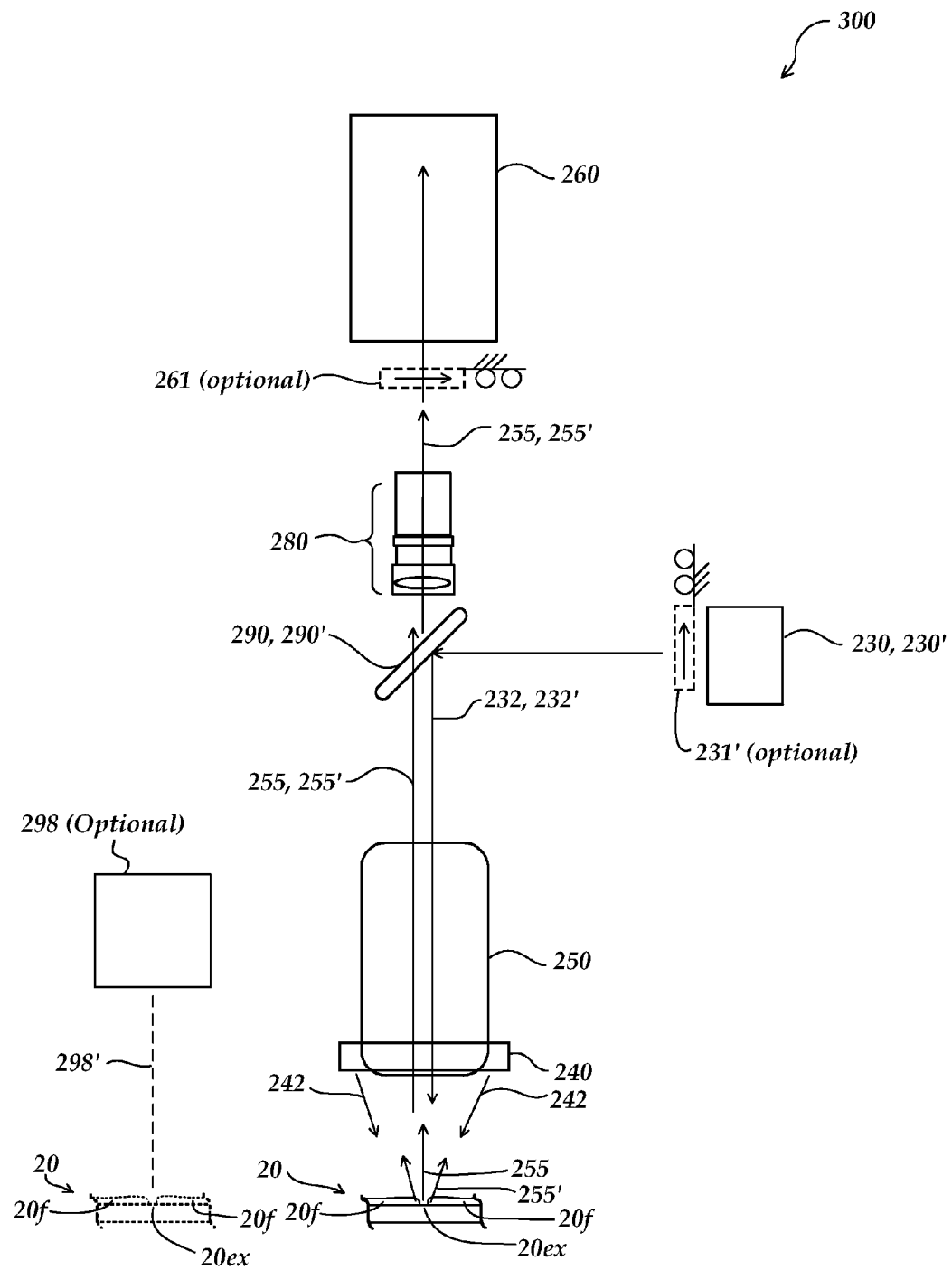
FIG. 3 is a diagram showing further details of portions of the vision components portion of the machine vision inspection system of FIG. 2.

FIG. 3 is a schematic diagram 300 showing one embodiment of controllable lighting elements of the vision components portion 200 (shown in FIG. 2), as well as one embodiment of the surface height sensor 298. In addition to elements shown in FIG. 2, the diagram 300 shows an optional excitation illumination filter 231' and an optional fluorescent imaging filter 261' which may be included to enhance controllable lighting usable in various methods disclosed herein. In addition, the workpiece 20 is shown to include a fluorescent material 20f, and an exposed portion 20ex, which is not covered by the fluorescent material 20f. As previously outlined, the coaxial light 230' may emit source light 232' which has an "excitation wavelength profile" which causes the fluorescent material 20f to fluoresce. The fluorescent workpiece light 255' emitted from the fluorescent material 20f may be received by the camera system 260 to provide fluorescent images. The coaxial light 230 may emit source light 232, and/or the ring light 240 may emit source light 242, which in the most versatile embodiments may each have a "non-excitation wavelength profile" which does not cause the fluorescent material 20f to significantly fluoresce, although this is not necessary in all embodiments. In any case, since the exposed portion 20ex does not include fluorescent material, in various configurations any source light (e.g., the source light 232, 242, and/or 232') reflected from the exposed portion 20ex may be received by the camera system 260 to provide non-fluorescent images of at least the exposed portion, even if the source light includes excitation wavelengths.

In many applications, reflected light may be much stronger than the emitted fluorescent light. Fluorescent images may therefore be enhanced in some embodiments by using an optional excitation illumination filter 231' to filter the excitation wavelengths provided by the source 230', and further narrow the band of the excitation wavelength profile in the light 232' to those which are most effective in stimulating the fluorescence. In addition, in some embodiments, the half-silvered minor 290 may include an optional dichroic filter 290' (e.g., a thin film filter), which is designed to reflect as much as possible of the narrowed excitation wavelength profile, and pass other wavelengths. Thus, any of the excitation wavelengths that are reflected from the workpiece 20 are substantially blocked from reaching the camera system 260 when a fluorescent image is desired. The optional excitation illumination filter 231' may be movable, and positioned such that it does not filter the content of the source light 232 from the source 230 when source light 232 is used to provide non-fluorescent images.

Alternatively, or in addition to the foregoing fluorescent imaging means, an optional fluorescent imaging filter 261' may be used to prevent all wavelengths other than emitted fluorescent imaging wavelengths from contributing to images in the camera system 260. In principle, the fluorescent imaging filter 261' may provide usable fluorescent images even if a significant amount of source light is reflected from the workpiece 20. However, it will block non-fluorescent image light. Therefore, the optional excitation illumination filter 231' is movable, and positioned such that it does not filter the reflected light when the system is used to provide non-fluorescent images.

Based on the foregoing, it will be understood that the clearest fluorescent images will be provided most easily when only an excitation wavelength profile is output to image the workpiece (e.g., from the source light 232'). Conversely, the clearest non-fluorescent images will be provided most easily when only a non-excitation wavelength profile is output to image the workpiece (e.g., from the source light 232 or 242).

It will be appreciated that the specific features and elements outlined above for the optical paths providing the source light for fluorescent and non-fluorescent imaging are exemplary only and not limiting. Numerous alternatives for illumination and/or imaging in a manner compatible with the methods disclosed herein will be apparent to one of ordinary skill in the art.

As described in greater detail below, in order to determine a repeatable and reliable focus height for fluorescent images of workpiece features located within a fluorescent material, the height of an exposed portion of the workpiece (that is, a portion that is not covered with a fluorescent material) such as the exposed portion 420*ex* may be determined, and the fluorescent imaging focus height may be determined with reference to that determined height of the exposed portion. This may be more reliable than focusing based on a fluorescent image, for example. In some embodiments, the height of the exposed portion may be determined based on the height corresponding to the best contrast in a set of autofocus images distributed along the Z axis direction. However, in other embodiments, as shown in FIG. 3, the machine vision inspection system may comprise an optional surface height sensor 298, and the system may be configured with the exposed portion 420*ex* positioned within a working range of the surface height sensor 298, which may be operated to use its schematically illustrated height sensing means 298' to determine the height of surface portion exposed portion 420*ex* along the Z axis or focus direction. In some embodiments, the surface height sensor 298 may comprise a touch probe sensor, and the height sensing means 298' may comprise its touch probe stylus. In other embodiments, the surface height sensor 298 may comprise an optical triangulation type sensor, e.g., a triangulation sensor wherein a height relationship relative to a surface determines the position of a reflected light beam (which may provide the sensing means 298') on a light sensitive detector of the sensor. In other embodiments, the surface height sensor 298 may comprise a focus signal sensor, e.g., a focus signal sensor wherein a height relationship relative to a surface determines the path of a reflected light beam (which may provide the sensing means 298') through a lens and to a location on a light sensitive detector of the sensor. In any case, such sensors may be used to provide a determined height for the exposed portion 20*ex* in various embodiments of the methods disclosed herein, according to known techniques.

Figure 4:
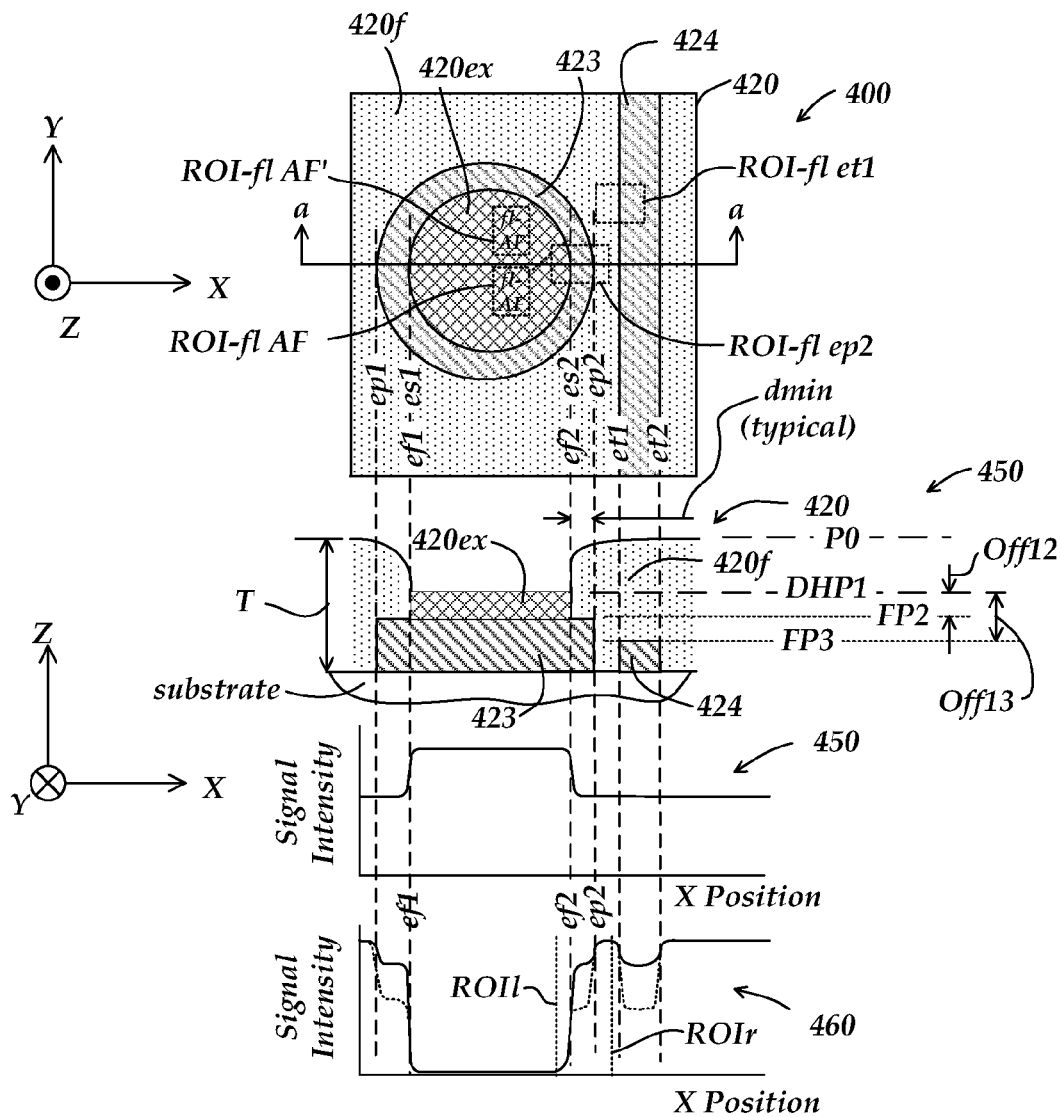
FIG. 4 shows a top view and a cross section view of features on a representative workpiece aligned with signal intensity profiles along a scan line through a non-fluorescent image of the features and a fluorescent image of the features.

FIG. 4 shows a top view 400 of a field of view of the machine vision inspection system which shows the features of a representative workpiece portion 420 and a cross section view 450 along a cross section a-a (a-a shown in view 400) of the features on the representative workpiece portion 420. Some dimensions are exaggerated in FIG. 4, for clarity of illustration. The upper coordinate axes correspond to the top view 400 and the lower coordinate axes correspond to the cross section view 450. Aligned below views 400 and 450 are corresponding signal intensity profiles 450 and 460. Each of the signal intensity profiles 450 and 460 represent the intensity variation along a scan line through an image of the features in a non-fluorescent image (e.g., an image illuminated with a first "non-excitation" wavelength profile) and a second fluorescent image of the features (e.g., an image illuminated with a "fluorescent excitation" wavelength profile), respectively. Thus, the signal intensity profile 450 is for a conventional image, and the signal intensity profile 460 is for a fluorescent image. The scan line is located in each image to correspond to the location of section a-a, in this example. As outlined with reference to FIG. 3, the first wavelength profile may be provided by one or both of the source lights 232 and/or 242 (and/or reflected light arising from source light 232', in some embodiments), and the excitation wavelength profile may be provided by source light 232'. The representative workpiece portion 420 may in some instances be part of a representative workpiece used for creating a part program in a learn mode, or in other instances a workpiece undergoing inspection operations in a run mode.

The features shown in views 400 and 450 include a substrate, a solder resist layer 420*f*, also referred to as a fluorescent material 420*f* (shown with a dotted fill), having edges at X axis locations ef1 and ef2; a conductive pad 423 (shown with a parallel line fill) having edges at X axis locations ep1 and ep2; an exposed portion 420*ex* (e.g., an exposed plated or soldered portion of the pad 423, shown with a crosshatch fill) having edges at X axis locations es1 and es2; and a conductive trace 424 (shown with a parallel line fill) having edges at X axis locations et1 and et2. The exposed portion 420*ex* may simply be an exposed portion of the conductive pad 423 when the conductive traces of a printed circuit board are not plated or soldered at the time of inspection. View 400 also shows an edge detection video tool (edge tool, for short) region of interest ROI-fl ep2 and an associated autofocus video tool (autofocus tool, for short) region of interest ROI-fl AF, and an edge tool region of interest ROI-fl et1 and associated autofocus video tool (autofocus tool, for short) region of interest ROI-fl AF', described in greater detail below. As is generally known in the art, such regions of interest (ROI's) may be sized and located on an image to define the extent of the image which is to be analyzed using image processing operations which are part of the associated video tool. According to convention, the ROI of a video tool (e.g., ROI-fl ep2) may also refer to all the operations of the associated video tool, not simply its region of interest, and the meaning will be clear based on the context of such reference.

FIG. 4 is an example of relatively "ideal" fabrication. The edges of the solder resist layer 420*f* coincide with the edges of the exposed portion 420*ex*, as may be the case if the exposed portion is not plated or if the plating or solder is applied through a pre-existing solder resist layer 420*f*. The solder resist layer 420*f* overlaps and insulates the conductive pad 423 all around its periphery, and also fully insulates the conductive trace 424. A representative example of a minimum desirable insulating "overlap" width dmin (typical) for the solder resist layer 420f relative to the edge of the adjacent conductive element is shown between the edges ef2 and ep2. More generally, the overlap dmin is desired all along each conductive element edge, to prevent unwanted electrical shorts between conductive elements. In some applications, dmin may be on the order of 10 microns, or even less. The solder resist layer 420f has a thickness dimension T. In some applications, the thickness T may be on the order of 25-150 microns, or more, which may cause the solder resist layer 420f to significantly obscure the imaged edge ep2.

It may be desired to inspect dmin at several representative locations, in order to insure that the pattern of the solder resist layer 420f is properly registered relative the pattern of conductive elements. This may require reliably automatically imaging and/or locating the edges of the conductive elements with an accuracy of less than 10 microns through a relatively thick translucent fluorescent material layer, which is a difficult problem. Related issues are discussed with reference to profiles 450 and 460.

As previously indicated, the signal intensity profiles 450 and 460 represent the intensity variation along a scan line at the location a-a in conventional image, and a fluorescent image, respectively. For example, the signal intensity profile 450 results from reflected image light from the surfaces of the fluorescent material 420f and the exposed portion 420ex. The signal intensity profile 450 shows intensity changes at the locations of the edge es1 and/or ef1, and the edge es2 and/or ef2. If the image which provides the signal intensity profile 450 is autofocused based on the autofocus tool ROI-AF located on the exposed portion 420ex, then the focus plane for the image will be approximately the determined height plane DHP1, and the edges es1 and es2 may primarily determine the location of the intensity changes. If the image which provides the signal intensity profile 450 is autofocused based on an autofocus tool ROI (not shown) located on a surface of the fluorescent material 420f (e.g., on the plane P0), then the focus plane for the image may be closer to the plane P0, and the edges ef1 and ef2 may primarily determine the location of the intensity changes. However, if the fluorescent material 420f is translucent, in some cases it may produce inaccurate and/or unreliable autofocus results. Nevertheless, in either case, the associated edge locations may be determined based on the intensity changes according to known methods (e.g., at the locations of the maximum rate of intensity change). However, features (e.g., edges) located within the fluorescent material 420f may produce little or no signal in the conventional reflected light image used for the signal intensity profile 450. In contrast, a fluorescent image may indicate such obscured features, as shown in the signal intensity profile 460.

Elements and operations usable to acquire a fluorescent image have been previously outlined with reference to FIG. 3 (e.g., the fluorescent material 420f fluoresces to provide fluorescent image light when excited by the source light 232'). For purposes of discussion, the signal intensity profile 460 includes a solid signal line indicating the intensity signal derived from a fluorescent image focused at the determined height DHP1, and a dotted signal line showing an intensity signal variation observed in a different fluorescent image focused at one of focus heights FP2 or FP3. This illustrates a significant problem associated with determining the location of features located within a fluorescent material in a fluorescent image.

In particular, the fluorescent image signal intensity is potentially influenced at various locations by factors including the amount of the diffuse fluorescent light emitted throughout the thickness of the fluorescent material 420f at that particular location, and the reflection of the fluorescent light by the workpiece features located within the fluorescent material proximate to that location, as well as by the image focus height and its relationship to the Z height range of the fluorescent material 420f and the Z height of the surface(s) adjacent to the features within the fluorescent material (e.g., the Z height of the conductive pad 423). Thus, in signal intensity profile 460 the example of the intensity signal provided at a focus height set at DHP1 (the solid line), there is a maximum signal where the fluorescent material 420f is thickest, and a minimum signal where there is no fluorescent material 420f. At the focus height set at DHP1 (the solid line), there is some drop from the maximum in the signal at edges ep1, ep2, et1, and et2. However, because the image determined height plane DHP1 is distant from the surface of the conductive pad 423 and conductive trace 424, the effects associated with them are blurred and the signal drop is not strong. Edge detection based on the associated signal changes may be less reliable and less accurate, or even impossible. For example, the left and right edges of the ROI-fl ep1 are indicated by the limits ROIl and ROIr in signal intensity profile 460, and the intensity change indicated by the solid line at the edge ep2 is not large. If the edge tool ROI-fl ep1 is trained to find this weak edge in a fluorescent image that is not optimally focused for this edge feature (that is, if the video tool edge detection parameters are determined based on this representative signal, and stored in a part program for inspecting edges on similar parts, according to known video tool methods), the resulting part program may not operate reliably. It will be appreciated that the results might be even worse if the focus plane were higher in the fluorescent material 420f, or at its surface (e.g., the plane P0). In contrast, in profile 460 the example of the intensity signal provided at a focus height set at FP2 or FP3 (including the signal deviations indicated by the dotted signal lines), there is a more significant drop in the signal at edges ep1, ep2, and et1, because the image focus plane is located relative to the surface of the conductive pad 423 and conductive trace 424 such that the effects associated with them are either more effective on the intensity signal, or less blurred in the fluorescent image, or both. Video tool edge detection parameters that are determined and stored in a part program based on this representative signal (e.g., derived from an optimally focused fluorescent image), may be relatively more reliable and more accurate. It is desirable in most applications that the fluorescent imaging height is determined such that it best enhances the detection of the desired feature located within the fluorescent material in the resulting fluorescent image. In some embodiments, a window in a graphical user interface of the machine vision inspection may display an intensity signal profile analogous to the profile 460, so that the best fluorescent imaging height may be more easily judged by a user. Alternatively, such a signal profile may be automatically evaluated as a function of height, to determine the fluorescent image focus height that provides the maximum intensity signal slope in the vicinity of the desired edge.

It should be appreciated that although the signal is shown to drop above the conductive pad 423 and conductive trace 424 in this example, for a different color or reflectivity or possible fluorescence in the substrate, or for an edge feature of a material different than these conductive elements, the signal might increase at the edges of the edge feature. However, analogous focus-dependent amounts of edge-indicating signal change may still be observed.

As outlined above, the focus plane of a fluorescent image may be an important factor in providing repeatable and accurate detection of the location of obscured features beneath a fluorescent material layer. For tight feature tolerances (e.g., 10 microns) this factor may become critical. However, autofocusing using fluorescent images is unreliable, in that autofocusing is usually done based on image contrast metrics and the highest contrast image height for a fluorescent image may be unreliable due to variations in the flatness, thickness, bubble content, particulate content, and particular obscured features in a fluorescent material layer. This is especially problematic when learning machine vision inspection operations and tool parameters (e.g., in learn mode) using a representative workpiece and then attempting to inspect a similar workpiece using identical operations, in that the tolerances and fabrication control related to fluorescent coatings may be relatively poor in comparison to many other materials and fabrication processes used in miniature precision devices. Therefore, it is desirable to provide a focus height for fluorescent images according to more repeatable methods as disclosed herein.

For example, in various embodiments of a method that provide a reliable focus height for fluorescent images, the height of an exposed portion (that is, a portion that is not covered with a fluorescent material) of a workpiece such as the exposed portion 420*ex* may be determined, in order to provide a reliable reference height. That reference height may then be used as the basis for focusing a fluorescent image. In some embodiments, a height sensor such as the surface height sensor 298 may be used to determine the exposed portion height as outlined previously. However, in other embodiments, the surface height sensor 298 may be omitted and/or the height of the exposed portion height portion may be determined by performing an autofocus operation on the exposed portion, using illumination and imaging methods outlined with reference to FIG. 3, and/or further below. When the determined height of the exposed portion 420*ex* is determined by an autofocus operation, the autofocus height may be based on the height of best image contrast for the exposed portion 420*ex* as indicated by a set of non-fluorescent autofocus images (e.g., "non-fluorescent" at least at the location of the exposed portion), then that focus height determined based on the exposed portion (e.g., its "best focus" height, or at least a well-focused height) may be the determined height that is used as the basis for a fluorescent imaging focus height.

In one embodiment, the determined height based on the exposed portion (e.g., its focus height) may be used as the fluorescent imaging focus height or plane, particularly if the height of the exposed portion is close to the height of the surface adjacent to the edge feature to located in the fluorescent image. In other applications, it may be desirable to use the determined height based on the exposed portion as a reference height (that is, a height that bears a relatively predictable height relationship to a height of the fluorescent material, or to the surface having the edge feature located in the fluorescent material) and use a fluorescent imaging focus height or focus plane that is offset by a defined distance from this reference height.

For example, FIG. 4 shows that the focus plane FP2 is offset from the Z height of the determined height plane DHP1 by a defined Z offset Off12. The focus plane FP2 may be more appropriate for acquiring a fluorescent image to be used for detecting the edge ep2 located in the edge tool ROI-fl ep2. A Z offset Off13 could be similarly established between DHP1 and FP3, if desired. The focus plane FP3 may be more appropriate for acquiring a fluorescent image to be used for detecting the edge et1 located in the edge tool ROI-fl et1. However, the best offset to use for any particular edge detection may more generally be determined or confirmed by a user during learn mode on a representative workpiece, and stored in a part program as a parameter associated with acquiring the associated fluorescent image for edge detection during run mode.

For example, the Z height where a desired feature within the fluorescent material (e.g., an edge) is well defined by an intensity change in a fluorescent image may be manually or automatically determined, and the determined Z height corresponding to the exposed portion (e.g., as determined by a height sensor or an autofocus operation) may be determined, and the Z offset between those heights may be determined and stored in the part program during learn mode. Then, during run mode, the fluorescent imaging height for the corresponding edge feature may be determined based on the height of the corresponding exposed portion (e.g., as determined by a height sensor or an autofocus operation), moving by the stored Z offset to establish a fluorescent imaging height in relation to the determined height of the exposed portion, and obtaining a fluorescent image at that fluorescent imaging height, to be used for determining the location of the edge within the fluorescent material. In various embodiments, the offset is advantageously determined such that the fluorescent imaging height falls within the layer of fluorescent material.

In some applications, it is most advantageous to determine the height of an exposed portion that is selected to have a surface height that falls within the height dimension of the fluorescent material that covers the feature that is to be imaged at the fluorescent imaging height. In some applications, it is most advantageous to determine the height of an exposed portion that is selected to have the same surface height as the surface of a material layer that has an edge feature within the fluorescent material that is to be imaged at the fluorescent imaging height. In some such embodiments, it may be adequate if the fluorescent imaging height is simply set to be the same as the determined height of the exposed portion. However, it will be appreciated that such specific choices for the exposed portion and the fluorescent imaging height are not limiting, and may not be possible or optimal for all workpieces or applications.

For some workpieces, the thickness and/or composition of the fluorescent material layer may be highly variable. Thus, in some embodiments it may be desirable to determine a fluorescent image height based on more information about such variations, in addition to a reference height established based on the exposed portion as outlined above. For example, the height of the surface of the fluorescent material 420*f*, and/or its thickness may be established (e.g., based on surface height sensor measurements, or autofocus operations that use non-fluorescent imaging, or other known methods). Then the Z offset outlined above may be determined based at least partly on this additional information (e.g., as a proportion of the thickness in relation to the determined height of the exposed portion, or another desired relationship).

In some applications, the location of the feature within the fluorescent material is the desired inspection information and may be determined based on the fluorescent image (e.g., by identifying the location of the edge ep2 using the edge tool ROI-fl ep2). In other applications, the dimension dmin is the desired inspection information and may be determined based on identifying the location of the edge ep2 in the fluorescent image, and determining the location of the edge ef2 in either a fluorescent image or a non-fluorescent image (e.g., using another edge tool) and determining the difference between their locations.

In some embodiments, the video tools shown in FIG. 4 may be known types of edge detection tools and autofocus tools, which are implemented along with known motion operations and programming statements and the like, in a sequence that performs operations according to the methods disclosed herein. In other embodiments, the video tools shown in FIG. 4 may be new types of video tools specific to fluorescent image edge detection. For example, in one embodiment, a user may select the video tool ROI-fl ep2 from a tool bar in a user interface, which may cause the user adjustable ROI of ROI-fl ep2 to appear on a real time video image (e.g., appearing as 420), along with the "linked" autofocus ROI of ROI-fl AF. The video tool may be configured such that the user can drag and size the ROI of ROI-fl et1 on a desired exposed portion and execute it to autofocus using reflected light (e.g., as outlined previously). In one embodiment, the video tool may be configured to then implement a fluorescent imaging configuration and display a fluorescent image at the current focus height. The user may then drag and size the ROI of ROI-fl ep2 on a desired edge, and also vary the focus height if the current focus height does not produce a desirable edge image. The edge tool parameters may then be trained using the best fluorescent image, and trained edge parameters and the current Z offset relative to the determined height of the associated exposed portion may be stored in the part program for later use inspecting similar workpieces. The video tool(s) ROI-fl et1 and ROI-fl AF' may be similarly associated and trained, or in one embodiment the video tool ROI-fl et1 may be configured to use previously determined "exposed portion" parameters associated with ROI-fl AF if it is located in the same field of view, and the video tool portion ROI-fl AF' may be omitted. Other video tool embodiments and associated graphical user interface features will be apparent to one of ordinary skill in the art having the benefit of the general teachings disclosed herein.

Figure 5A:
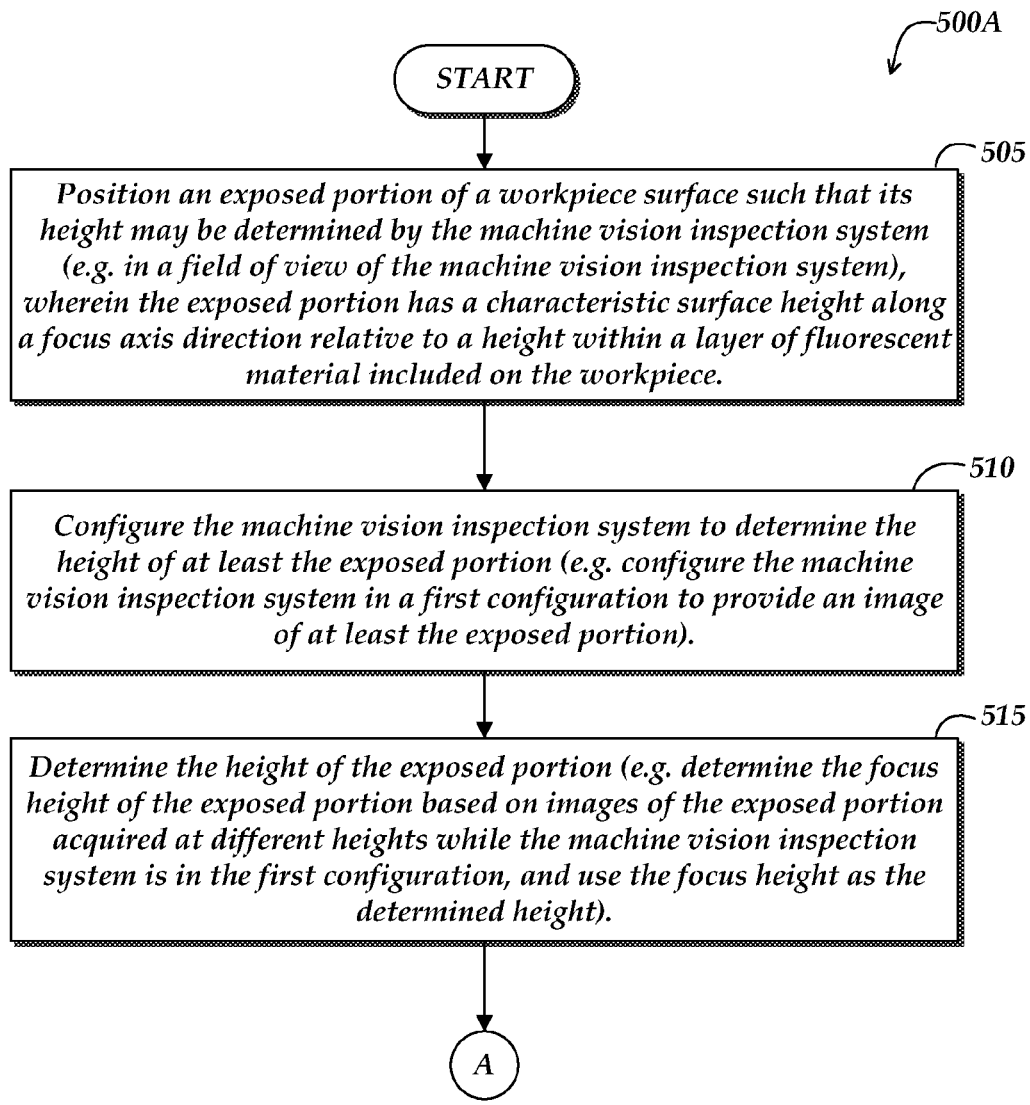
FIGS. 5A and 5B show flow diagrams outlining a method and routine for operating a machine vision inspection system to determine a reliable and repeatable fluorescent imaging height.
Figure 5B:
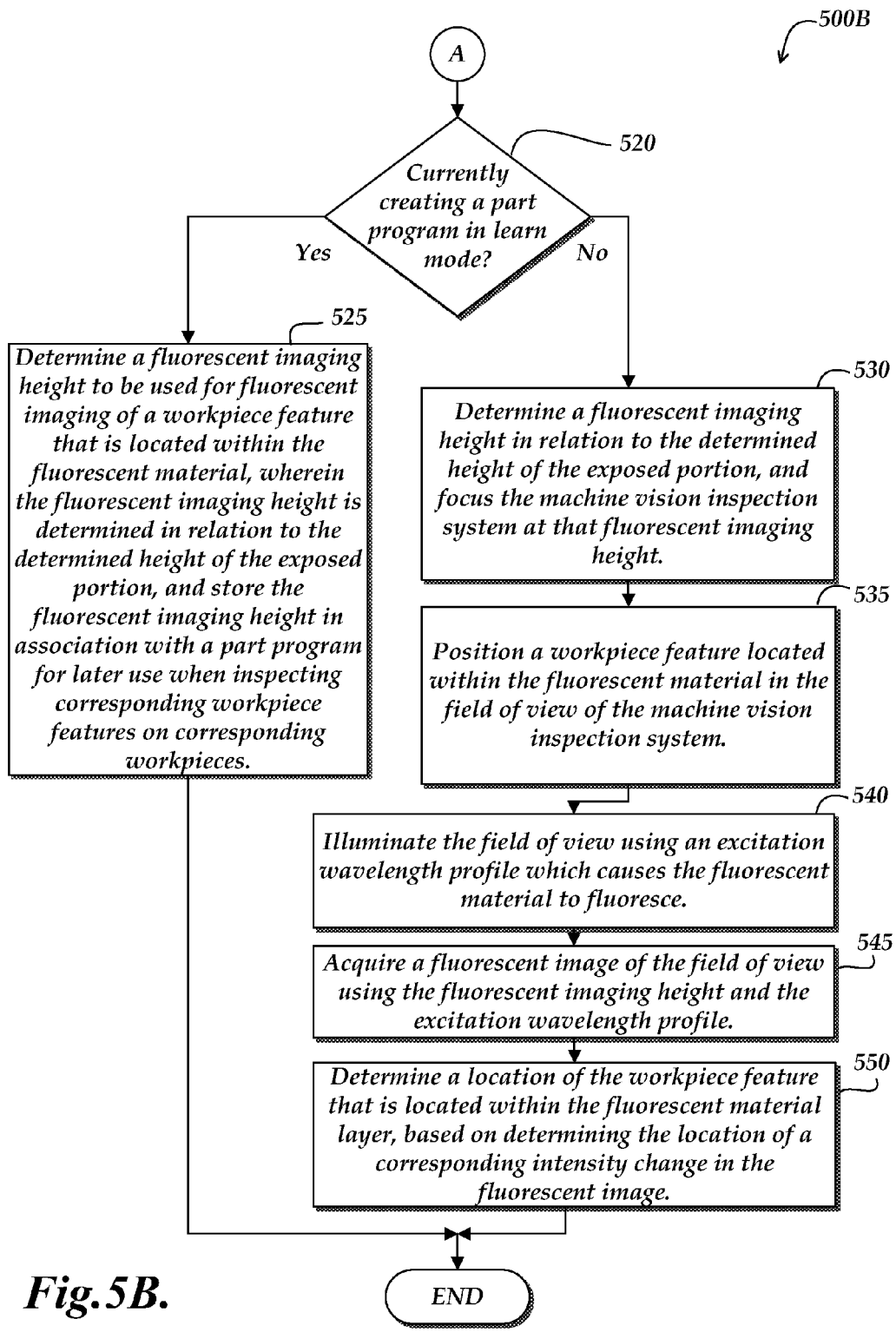

FIGS. 5A and 5B show flow diagrams 500A and 500B outlining a method for operating a machine vision inspection system to determine a reliable and repeatable fluorescent imaging height, such as may be used for acquiring a fluorescent image for inspecting the location of a workpiece edge that is located within a layer of fluorescent material.

In one embodiment, the method shown in FIGS. 5A and 5B may be implemented, at least in part, by a user by selecting and operating the fluorescent image edge detection tool 143*fl* shown in FIG. 2 and/or as described with reference to one embodiment of the edge tool ROI-fl ep2 shown in FIG. 4. In other embodiments, the method may be implemented using various known tools and/or programming operations.

The method starts, and at a block 505, an exposed portion of a workpiece (that is, a portion that is not covered by a fluorescent material) is positioned such that its height may be determined by the machine vision inspection system, wherein the exposed portion has a characteristic surface height along a focus axis direction (e.g., the Z axis direction) relative to a height within a layer of fluorescent material included on the workpiece. In some embodiments wherein the machine vision inspection system includes a surface height sensor, this may comprise positioning the exposed portion in a working range of the surface height sensor. In some embodiments, this may comprise positioning the exposed portion in a field of view of a machine vision inspection system (e.g., for an autofocusing operation). In various applications the exposed portion may be selected to have a surface height above, within, or below a height range of the fluorescent material. When a bare PCB is the workpiece, the exposed portion of the workpiece may comprise an exposed portion such as the exposed portion 420*ex* shown in FIG. 4, which may be a plated or soldered portion or a conductive pad such as conductive pad 423, or an exposed portion of a substrate or an installed component, or the like.

At a block 510, the machine vision inspection system is configured to determine the height of at least the exposed portion. In some embodiments wherein the machine vision inspection system includes a surface height sensor, this may comprise configuring the machine vision inspection system to use the surface height sensor to determine the height of the exposed portion. In some embodiments, this may comprise configuring the machine vision inspection system in a first configuration to provide an image of at least the exposed portion (e.g., configuring illumination, etc., for an autofocusing operation). In such embodiments, in images acquired using the first configuration at least the exposed portion produces a non-fluorescent image, as outlined above with reference to FIG. 3. In some embodiments, in the first configuration the field of view may be illuminated using a first "non-exciting" wavelength profile which does not cause significant fluorescence in the fluorescent material. Various alternative embodiments and considerations related to configuring the machine vision inspection system to determine the height of the exposed portion have been outlined previously (e.g., with reference to FIG. 3).

At a block 515, the height of the exposed portion is determined. In some embodiments wherein the machine vision inspection system includes a surface height sensor, this may comprise using the surface height sensor to determine the height of the exposed portion. In some embodiments, this may comprise determining a focus height of the exposed portion based on images of the exposed portion acquired at different heights while the machine vision inspection system is in the first configuration outlined above, and using that focus height as the determined height of the exposed portion. Such a focus height where the exposed portion is well focused may be determined by known methods (e.g., by analyzing image contrast as a function of Z height). Various considerations related to selecting the exposed portion to be used at block 515 have been outlined previously (e.g., with reference to FIG. 4). The flow diagram 500A continues through a block A, shown in FIGS. 5A and 5B.

FIG. 5B shows operations that determine a desirable fluorescent imaging height to be used for fluorescent imaging of workpiece feature located within the fluorescent material, wherein the fluorescent imaging height is determined in relation to the determined height of the exposed portion (e.g., as determined above). The decision block 520 indicates whether the fluorescent imaging height is being determined and stored for the first time (e.g., during learn mode) or whether the fluorescent imaging height is being determined in run mode, based on previously stored information. In particular, at the decision block 520, if operations are being performed to create a part program in learn mode, then the routine continues to a block 525, otherwise (e.g., during run mode) the routine continues to a block 530, as described further below. At the block 525, a fluorescent imaging height to be used for fluorescent imaging of a workpiece feature located within the fluorescent material is determined—in relation to the determined height of the exposed portion for reasons previously described, and the fluorescent imaging height is stored in association with a part program for later use (e.g., when acquiring a fluorescent image that is used for inspecting corresponding workpiece features on corresponding workpieces). In some embodiments of the operations at block 525 the fluorescent imaging height may be stored in the form of an offset dimension relative to the previously determined height of the exposed portion, or as otherwise outlined herein.

At the block 530 (e.g., if a part program is currently being executed in run mode), a fluorescent imaging height for an associated feature located within the fluorescent material of the current workpiece is determined in relation to the determined height of the exposed portion of the current workpiece (established previously during run mode), and the machine vision inspection system is focused at that fluorescent imaging height. Thus, at block 530, determining the fluorescent imaging height may comprise recalling fluorescent imaging height information stored in association with a current feature to be inspected in a part program, and determining the fluorescent imaging height in relation to the determined height of the exposed portion based on that information. Various considerations and alternative embodiments related to the fluorescent imaging height have been outlined previously (e.g., with reference to FIGS. 3 and 4).

The routine continues at block 535, where the workpiece feature (e.g., an edge feature) that is located within the fluorescent material layer and is associated with the current fluorescent imaging height is positioned in the field of view of the machine vision inspection system. Then, at a block 540 the field of view is illuminated using an excitation wavelength profile which causes the fluorescent material to fluoresce, and at a block 545 a fluorescent image of the field of view is acquired using the fluorescent imaging height and the excitation wavelength profile. Various considerations and alternative embodiments related to excitation illumination and fluorescent imaging have been outlined previously (e.g., with reference to FIGS. 3 and 4).

Next, at a block 550, a location of the workpiece feature that is located within the fluorescent material layer is determined, based on determining the location of a corresponding intensity change in the fluorescent image acquired at block 545, and the routine ends. For example, with reference to FIG. 4, the edge ep2 may be determined based on the intensity change along the scan line at the location a-a in the region of interest of the edge tool ROI-fl ep2, as indicated in the profile 460. In one embodiment, the intensity change may be detected as the location of the maximum intensity slope or gradient in the vicinity of the edge ep2 (e.g., the vicinity may be indicated by a parameter of the edge tool ROI-fl ep2), according to known methods.

It should be appreciated that the methods disclosed herein provide a more reliable and repeatable fluorescent imaging height than previously practiced methods, and may be used for acquiring a fluorescent image for accurately and repeatably determining the location of a workpiece edge that is to be inspected within a fluorescent material. In addition, the methods may provide accuracy and repeatability at a higher speed than that which is available when using conventional fluorescent microscopy focusing techniques. While various preferred and exemplary embodiments of the invention have been illustrated and described, it will be appreciated that various changes can be made therein without departing from the spirit and scope of the invention.

The invention claimed is:

1. A method for operating a machine vision inspection system to determine a fluorescent imaging height for acquiring a fluorescent image for repeatably determining the location of a workpiece feature edge that is located within a layer of fluorescent material on a workpiece, the method comprising:
 (a) positioning an exposed portion of a surface of the workpiece such that its height is able to be determined by the machine vision inspection system, wherein the exposed portion is not covered by the layer of fluorescent material and has a characteristic surface height along a focus axis relative to a height within the layer of fluorescent material;
 (b) configuring the machine vision inspection system to determine the height of the exposed portion;
 (c) determining the height of the exposed portion;
 (d) using the determined height of the exposed portion, determining a fluorescent imaging height to be used for fluorescent imaging of the workpiece feature edge that is located within the layer of fluorescent material and is covered by the fluorescent material, wherein the fluorescent imaging height is determined in relation to the determined height of the exposed portion; and
 performing at least one of (e) and (f), wherein (e) comprises:
 (e) storing the determined fluorescent imaging height in association with a part program for later use when acquiring a fluorescent image that is used for inspecting the workpiece feature edge that is located within the layer of fluorescent material and is covered by the fluorescent material,
 and (f) comprises:
 (f) using the fluorescent imaging height determined in relation to the determined height of the exposed portion during execution of a part program when acquiring a fluorescent image that is used for inspecting the workpiece feature edge that is located within the layer of fluorescent material and is covered by the fluorescent material.

2. The method of claim 1, wherein the workpiece is a representative workpiece and the method is performed in association with a learn mode of operation of the machine vision inspection system, which is used for creating a part program to be used for inspecting workpieces similar to the representative workpiece, and the method comprises performing the steps (a), (b), (c), (d) and (e).

3. The method of claim 2, further comprising:
 (g) positioning the workpiece feature edge that is located within the layer of fluorescent material in a field of view of the machine vision inspection system;
 (h) positioning the machine vision inspection system at the determined fluorescent imaging height;
 (i) illuminating the field of view using an excitation wavelength profile which causes the fluorescent material to fluoresce and output fluorescent imaging light;
 (j) acquiring a fluorescent image of the field of view using the fluorescent imaging height while illuminating the field of view using the excitation wavelength profile; and
 (k) determining a location of the workpiece feature edge that is located within the fluorescent material based on a location of a corresponding intensity change in the fluorescent image.

4. The method of claim 3, wherein step (k) comprises configuring the parameters of an edge detection video tool of the machine vision inspection system, and using that edge detection video tool in order to determine the location of the workpiece feature edge on the representative workpiece, and the method further comprises:
 (l) storing the configured parameters of the edge detection video tool in association with the part program, for later use to determine the location of the workpiece feature edge in fluorescent images of workpieces similar to the representative workpiece.

5. The method of claim 1, wherein the method is performed in association with a run mode of operation of the machine vision inspection system by executing a part program that includes inspecting the workpiece feature edge that is located within the fluorescent material on a workpiece that is similar to a representative workpiece used to create the part program, and the method comprises performing the steps (a), (b), (c), (d) and (f), wherein in step (d) determining the fluorescent imaging height to be used for fluorescent imaging of the workpiece feature edge comprises recalling fluorescent imaging height information stored in association with that workpiece feature edge in the part program, and determining the fluorescent imaging height based on that information.

6. The method of claim 5, comprising:
    (g) positioning the workpiece feature edge that is located within the layer of fluorescent material in the field of view of the machine vision inspection system;
    (h) positioning the machine vision inspection system at the determined fluorescent imaging height;
    (i) illuminating the field of view using an excitation wavelength profile which causes the fluorescent material to fluoresce and output fluorescent imaging light;
    (j) acquiring a fluorescent image of the field of view using the fluorescent imaging height while illuminating the field of view using the excitation wavelength profile; and
    (k) determining a location of the workpiece feature edge that is located within the fluorescent material based on a location of a corresponding intensity change in the fluorescent image.

7. The method of claim 6, wherein step (k) comprises configuring an edge detection video tool of the machine vision inspection system according to associated parameters stored in the part program, and using that edge detection video tool in order to determine the location of the workpiece feature edge in the fluorescent image.

8. The method of claim 6, further comprising:
    (l) determining the location of an edge of the layer of fluorescent material; and
    (m) determining a measurement of a dimensional relationship between the location of the edge of the layer of fluorescent material layer and the location of the workpiece feature edge that is located within the layer of fluorescent material.

9. The method of claim 8, wherein:
    the edge of the layer of fluorescent material is an edge included in the fluorescent image of the field of view acquired in step (j); and
    in step (l), determining the location of an edge of the layer of fluorescent material comprises locating the edge of the layer of fluorescent material in the fluorescent image acquired in step (j).

10. The method of claim 1, wherein the machine vision inspection system comprises a fluorescent imaging filter that blocks at least one wavelength of an excitation wavelength profile used as illumination when acquiring a fluorescent image and passes at least one wavelength of fluorescent imaging light emitted by the fluorescent material, and in step (j), acquiring the fluorescent image comprises using the fluorescent imaging filter to filter the image light used to form the fluorescent image.

11. The method of claim 1, wherein the fluorescent imaging height is determined as an offset dimension in relation to the determined height of the exposed portion.

12. The method of claim 1, wherein the fluorescent imaging height is determined such that it falls within the layer of fluorescent material.

13. The method of claim 1, wherein the exposed portion is selected such that it has a surface height that falls within a height dimension of the layer of fluorescent material.

14. The method of claim 13, wherein the exposed portion of the surface of the workpiece is selected such that it is nominally located at the same surface height as a surface of a material layer that has the workpiece feature edge that is located within the fluorescent material.

15. The method of claim 1, wherein:
    the machine vision inspection system comprises a surface height sensor comprising one of a touch probe type sensor, an optical triangulation type sensor, and a focus signal sensor;
    step (a) comprises positioning the exposed portion in a working range of the surface height sensor;
    step (b) comprises configuring the machine vision inspection system to use the surface height sensor to determine the height of the exposed portion; and
    step (c) comprises using the surface height sensor to determine the height of the exposed portion.

16. The method of claim 1, wherein:
    step (a) comprises positioning the exposed portion in a field of view of the machine vision inspection system;
    step (b) comprises configuring the machine vision inspection system in a first configuration to provide an image of at least the exposed portion; and
    step (c) comprises determining a focus height of the exposed portion based on images of the exposed portion acquired at different heights while the machine vision inspection system is in the first configuration and using that focus height as the determined height of the exposed portion.

17. The method of claim 16, wherein:
    the machine vision inspection system comprises controllable lighting that is controllable to output at least two wavelength profiles comprising:
        a non-excitation wavelength profile which illuminates the workpiece such that the workpiece provides primarily reflected image light and an insignificant amount of fluorescent light in response to the non-excitation wavelength profile, such that the non-excitation wavelength profile may be used to acquire non-fluorescent images, and
        an excitation wavelength profile which causes the layer of fluorescent material to fluoresce and output a significant amount of fluorescent imaging light such that the excitation wavelength profile may be used to acquire the fluorescent image; and
    in step (b), the first configuration includes configuring the controllable lighting to output the non-excitation wavelength profile and to not output the excitation wavelength profile.

18. The method of claim 17, wherein the controllable lighting comprises a ring light, and the first configuration includes outputting the non-excitation wavelength profile from the ring light.

19. The method of claim 17, wherein acquiring the fluorescent image includes configuring the controllable lighting to output the excitation wavelength profile and to not output the non-excitation wavelength profile.

20. A non-transitory computer-readable storage medium with instructions stored thereon that are executable by a processor in a machine vision inspection system to perform operations of:
    (a) positioning an exposed portion of a surface of a workpiece such that its height is able to be determined by the machine vision inspection system, wherein the exposed portion is not covered by a layer of fluorescent material and has a characteristic surface height along a focus axis relative to a height within the layer of fluorescent material;
    (b) configuring the machine vision inspection system to determine the height of the exposed portion;
    (c) determining the height of the exposed portion;

(d) using the determined height of the exposed portion, determining a fluorescent imaging height to be used for fluorescent imaging of a workpiece feature edge that is located within the layer of fluorescent material and is covered by the fluorescent material, wherein the fluorescent imaging height is determined in relation to the determined height of the exposed portion; and performing at least one of (e) and (f), wherein (e) comprises:

(e) storing the determined fluorescent imaging height in association with a part program for later use when acquiring a fluorescent image that is used for inspecting the workpiece feature edge that is located within the layer of fluorescent material and is covered by the fluorescent material, and (f) comprises:

(f) using the fluorescent imaging height determined in relation to the determined height of the exposed portion during execution of a part program when acquiring a fluorescent image that is used for inspecting the workpiece feature edge that is located within the layer of fluorescent material and is covered by the fluorescent material.

21. A machine vision inspection system for performing measurement operations on a workpiece, the machine vision inspection system comprising:

a memory for storing programmed instructions; and a processor configured to execute the programmed instructions to perform operations including:

(a) positioning an exposed portion of a surface of the workpiece such that its height is able to be determined by the machine vision inspection system, wherein the exposed portion is not covered by a layer of fluorescent material and has a characteristic surface height along a focus axis relative to a height within the layer of fluorescent material;

(b) configuring the machine vision inspection system to determine the height of the exposed portion;

(c) determining the height of the exposed portion;

(d) using the determined height of the exposed portion, determining a fluorescent imaging height to be used for fluorescent imaging of a workpiece feature edge that is located within the layer of fluorescent material and is covered by the fluorescent material, wherein the fluorescent imaging height is determined in relation to the determined height of the exposed portion; and performing at least one of (e) and (f), wherein (e) comprises:

(e) storing the determined fluorescent imaging height in association with a part program for later use when acquiring a fluorescent image that is used for inspecting the workpiece feature edge that is located within the layer of fluorescent material and is covered by the fluorescent material, and (f) comprises:

(f) using the fluorescent imaging height determined in relation to the determined height of the exposed portion during execution of a part program when acquiring a fluorescent image that is used for inspecting the workpiece feature edge that is located within the layer of fluorescent material and is covered by the fluorescent material.

* * * * *